Figure 1:
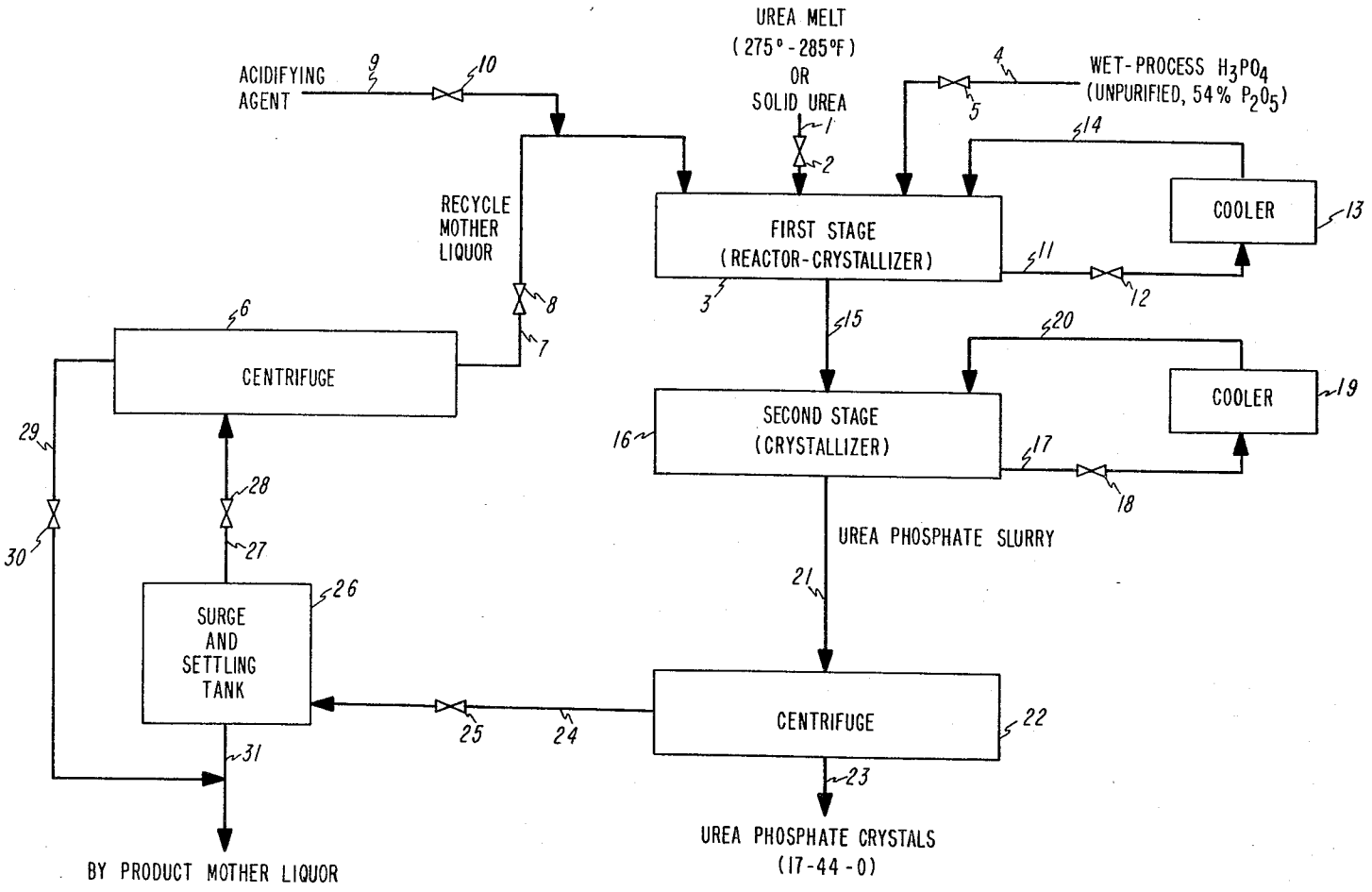
Figure 2:
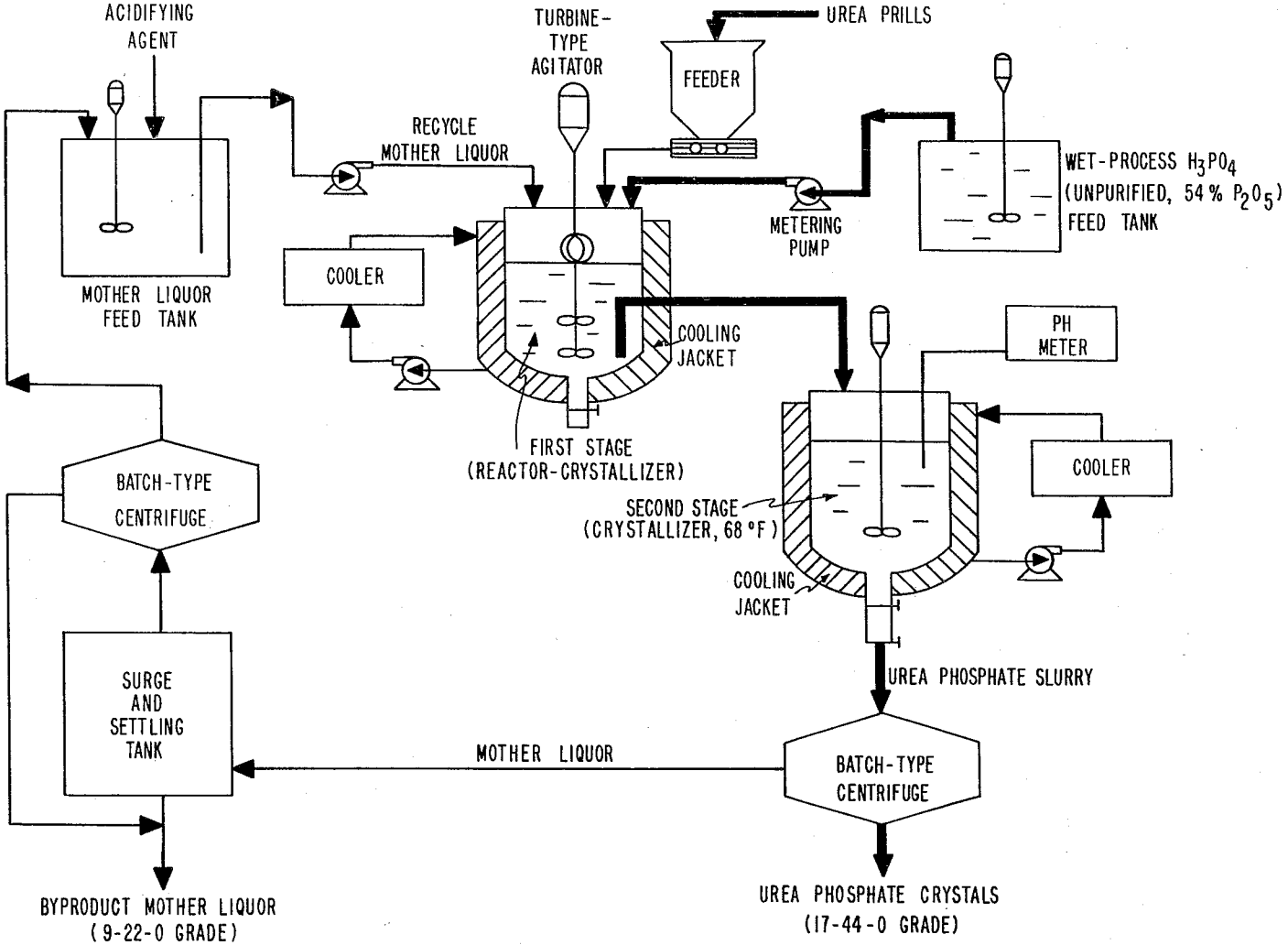
Figure 3:
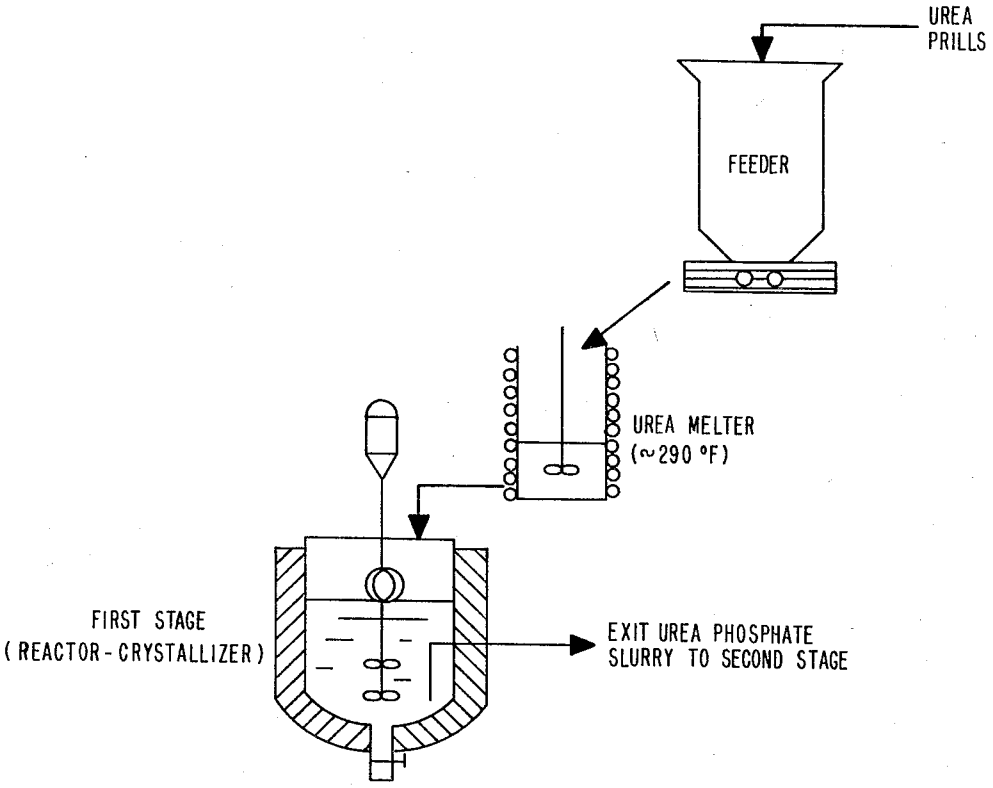
Figure 4:
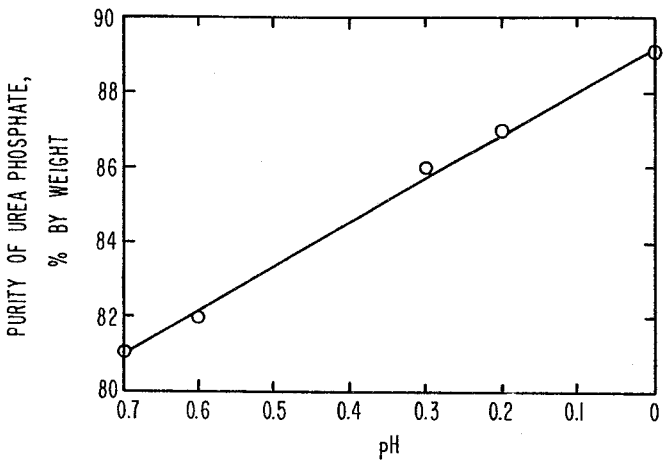

United States Defensive Publication [19] (H) [11] T103,206

Lewis et al. [43] Jul. 5, 1983

[54] PRODUCTION OF UREA PHOSPHATE

[76] Inventors: Harry T. Lewis, 802 Meadow La.; Ewell F. Dillard, Rte. 10, Box 196, both of Florence, Ala. 35630

[21] Appl. No.: 324,515

[22] Filed: Nov. 24, 1981

[51] Int. Cl.[3] ..... C07C 127/01; C07C 126/08

[52] U.S. Cl. ..... 564/363; 564/73

[57] ABSTRACT

A two-stage continuous crystallization process for production of urea phosphate by reaction of impure wet-process orthophosphoric acid (about 54 percent $P_2O_5$) and urea with simultaneous addition of a selected acidifying agent (sulfuric acid, hydrochloric acid, or phosphoric acid) to clarified mother liquor used as recycle in the process. Addition of the acidifying agent decreases pH in the crystallization process whereby the solubility of a contaminating water-insoluble iron phosphate-urea salt [$FeH_3(PO_4)_2.2CO(NH_2)_2$] is increased, purity of the crystalline urea phosphate product is improved significantly, and the useful storage life of the recycle mother liquor is prolonged.

8 Claims, 4 Sheets Drawing,

36 Pages Specification

The file of this unexamined application may be inspected and copies thereof may be purchased (849 O.G. 1221, Apr. 9, 1968).

PRODUCTION OF UREA PHOSPHATE FROM UREA AND MERCHANT-GRADE WET-PROCESS PHOSPHORIC ACID

APPARATUS USED IN BENCH-SCALE PRODUCTION OF UREA PHOSPHATE

BENCH-SCALE ADDITION OF UREA MELT TO FIRST STAGE

RELATIONSHIP OF PRODUCT PURITY VS. pH IN PROCESS